(12) United States Patent
Shibata (10) Patent No.: US 9,052,257 B2
(45) Date of Patent: Jun. 9, 2015

(54) METHOD OF TESTING RUBBER WEAR, AND METHOD, DEVICE AND PROGRAM OF CALCULATING RUBBER INDEX OF TIRE USING METHOD OF TESTING RUBBER WEAR

(75) Inventor: Tomonori Shibata, Kodaira (JP)

(73) Assignee: BRIDGESTONE CORPORATION, Tokyo (JP)

( * ) Notice: Subject to any disclaimer, the term of this patent is extended or adjusted under 35 U.S.C. 154(b) by 350 days.

(21) Appl. No.: 13/580,923

(22) PCT Filed: Feb. 24, 2011

(86) PCT No.: PCT/JP2011/054161
§ 371 (c)(1),
(2), (4) Date: Aug. 23, 2012

(87) PCT Pub. No.: WO2011/105498
PCT Pub. Date: Sep. 1, 2011

(65) Prior Publication Data
US 2013/0036791 A1   Feb. 14, 2013

(30) Foreign Application Priority Data
Feb. 24, 2010   (JP) .................................. 2010-039373

(51) Int. Cl.
*G01N 19/02* (2006.01)
*G01N 3/56* (2006.01)
*G01M 17/02* (2006.01)

(52) U.S. Cl.
CPC .............. *G01N 3/56* (2013.01); *G01M 17/022* (2013.01)

(58) Field of Classification Search
CPC ............................... G01N 3/56; G01M 17/022
USPC ........................................................ 73/8, 146
See application file for complete search history.

(56) References Cited

U.S. PATENT DOCUMENTS 2,293,344 A * 8/1942 Tobin et al. ..................... 73/146
2,367,838 A * 1/1945 Allen ................................ 73/7
(Continued)

FOREIGN PATENT DOCUMENTS

JP   3-48750 U    5/1991
JP   11-326144 A  11/1999
(Continued)

OTHER PUBLICATIONS

English Translation of JP 2008-185475, Aug. 14, 2008.*
(Continued)

*Primary Examiner* — Hezron E. Williams
*Assistant Examiner* — Alexander Mercado
(74) *Attorney, Agent, or Firm* — Sughrue Mion, PLLC (57) ABSTRACT

Provided is a method of testing rubber wear in which a wear phenomenon occurred in a tire can be precisely reproduced in a sample, and a method of calculating the rubber index of a tire using the method of testing rubber wear.

Also provided is a test method for predicting the anti-wear properties of a tire by using a test piece of the same rubber as that of a tire tread, which is a method of testing rubber wear in which, while a disk-shaped sample 3 and a disk-shaped grinding wheel 1 are rotated at individually predetermined numbers of rotations, the sample 3 is pressed on the outer periphery of the grinding wheel 1. A pressing load is applied to the sample 3 such that a contact pressure when the sample is pressed on the outer periphery of the grinding wheel 1 and a contact pressure at a site related to the evaluation of rubber wear of tread are the same.

6 Claims, 7 Drawing Sheets

(56) References Cited

U.S. PATENT DOCUMENTS

| | | | |
|---|---|---|---|
| 3,152,468 A * | 10/1964 | Powell | 73/8 |
| 6,212,947 B1 * | 4/2001 | Shimizu et al. | 73/146 |
| 6,263,728 B1 * | 7/2001 | Sumiya et al. | 73/146 |
| 6,269,690 B1 * | 8/2001 | Shimizu et al. | 73/146 |
| 2008/0228411 A1 * | 9/2008 | Miyashita et al. | 702/34 |

FOREIGN PATENT DOCUMENTS

| | | |
|---|---|---|
| JP | 2003-50190 A | 2/2003 |
| JP | 2005-227014 A | 8/2005 |
| JP | 2005-308447 A | 11/2005 |
| JP | 2006-232011 A | 9/2006 |
| JP | 2006-242697 A | 9/2006 |
| JP | 2008-82914 A | 4/2008 |
| JP | 2008-185475 A | 8/2008 |

OTHER PUBLICATIONS

International Search Report for PCT/JP2011/054161 dated May 24, 2011.

* cited by examiner

(B) Contact front end, Contact back end, K

METHOD OF TESTING RUBBER WEAR, AND METHOD, DEVICE AND PROGRAM OF CALCULATING RUBBER INDEX OF TIRE USING METHOD OF TESTING RUBBER WEAR

TECHNICAL FIELD

The present invention relates to a method of testing rubber wear, and a method, a device and a program of calculating the rubber index of a tire using the method of testing rubber wear, and more particularly to a method of testing rubber wear in which a wear phenomenon occurred in a tire can be precisely reproduced in a sample, and a method, a device and a program of calculating the rubber index of a tire using the method of testing rubber wear.

BACKGROUND ART

Since rubber used for rubber goods such as a tire wears during use, it is necessary for the goods to have high anti-wear properties, and therefore, development of a rubber material becomes important. In order to judge whether the developed rubber material is good or bad, it is necessary to evaluate the anti-wear properties of the rubber material. However, the evaluation of a practical wear life by practically using the rubber goods using the rubber material takes time, which suppresses the speed of the development.

Accordingly, a laboratory evaluation for evaluating wear life of rubber in a short time is widely performed. For example, Patent Document 1 discloses a rubber wear tester which comprises a disk-shaped grindstone, a grindstone rotating means which rotates the grindstone, a sample rotating means which rotates a disk-shaped rubber sample around an axis which is parallel to the rotation axis of the grindstone and a sample pressing means which presses sample on the grindstone, and provided with a sample rotation control means which controls the sample rotating means, wherein the sample rotation control means can be controlled in a control method in which the torque which rotates the rubber sample has a desired change pattern.

Patent Document 2 discloses a method of measuring the wear life of a tire, in which tire severity information specific to the travel condition and wear correspondence information specific to rubber of the same type of a tread rubber portion of the objective tire whose wear life is predicted, are acquired and each amount of rubber wear when abrasion energy that is determined based on the wear correspondence information and is equivalent to the energy quantity represented by each tire severity information, is used as an objective tire wear amount per unit time when the energy quantity represented by each tire severity information is applied to the objective tire, and in which equivalent tire wear total amount of the objective tire is determined when the objective tire is rolled over a specific rolling time range under the predetermined rolling condition, and equivalent wear life information indicating the wear life of the objective tire is determined and outputted based on the rolling distance range and equivalent wear total amount.

Further, Patent Document 3 discloses a wear test method in which, when a rubber sample is pressed on the outer periphery of a grinding wheel, a force in the circumferential direction of the wheel generated in the driving axle of the rubber sample is continuously measured, and the number of rotations of the driving axle of the rubber body sample is adjusted by feedback control such that the force in the circumferential direction generated in the driving axle approaches the predetermined value.

RELATED ART DOCUMENTS

Patent Documents

Patent Document 1: Japanese Unexamined Patent Application Publication No. 2008-185475
Patent Document 2: Japanese Unexamined Patent Application Publication No. 2008-82914
Patent Document 3: Japanese Unexamined Patent Application Publication No. 2006-242697

SUMMARY OF THE INVENTION

Problems to be Solved by the Invention

However, when the anti-wear properties of rubber is evaluated by the methods of evaluating rubber wear disclosed in Patent Documents 1 to 3, for example, in the case of rubber used for tread rubber of a tire, there is a case where a tire using the better rubber material of two rubber materials having different formulations in a laboratory evaluation is worse than a tire using the other rubber material when the tires fitted on a practical vehicle travel under practical use conditions. Therefore, a method of evaluating tire anti-wear properties using a sample have room for improvement of the prediction accuracy.

Accordingly, an object of the present invention is to overcome the above-mentioned problems and to provide a method of testing rubber wear in which a wear phenomenon occurred in a tire can be precisely reproduced in a sample, and a method, a device and a program of calculating the rubber index of a tire using the method of testing rubber wear.

Means for Solving the Problems

In order to solve the above-mentioned problems, the present inventor intensively studied focusing on a contact pressure which is an important factor for a friction phenomenon to discover the following findings. That is, in a conventional method of evaluating rubber wear, in the setting of a pressing load when a sample is pressed, a measure has been taken such that (1) the load is set to a contact pressure which is the same as the internal pressure of the tire, or such that (2) the load is adjusted to a contact pressure which is an averaged tire wheel load on an apparent contact patch area. It was, however, found that, since the surface of the tire has a curvature in the tire width direction and the surface is not in contact with a ground uniformly, and has a contact pressure distribution in the tire width direction in the contact patch, the contact pressures obtained by the above-mentioned methods (1) and (2) were different from the real contact pressure in the tire contact patch, and thus, the wear phenomenon of the tire could not be precisely reproduced in the sample.

Based on such findings, the present inventor further studied intensively to find that the above-mentioned problems can be overcome, thereby completing the present invention.

That is, the method of testing rubber wear of the present invention is a method of testing rubber wear by predicting the anti-wear properties of a tire with the use of a test piece of the same rubber as that of a tire tread, which is a method of testing rubber wear in which, while a disk-shaped sample and a disk-shaped grinding wheel are rotated at individually predetermined numbers of rotations, the sample is pressed on the outer periphery of the grinding wheel, wherein a pressing load is applied to the sample such that a contact pressure when the sample is pressed on the outer periphery of the grinding wheel and a contact pressure at a site related to the evaluation of rubber wear of a contact patch portion of the tire are the same.

In the present invention, it is preferred that a torque be applied to the disk-shaped sample such that a frictional energy generated when the disk-shaped sample is pressed on the outer periphery of the grinding wheel in a state in which the pressing load is applied and a frictional energy at a site related to the evaluation of rubber wear of a contact patch portion of the tire are the same.

A rubber index calculating method of a tire of the present invention comprises a tire frictional energy measurement step in which a tire frictional energy of a tire under plural tire input conditions which are provided to the tire is measured by a frictional energy measurement device which performs measurement based on the shearing force and the slippage of a tire contact patch, a contact pressure measurement step in which a contact pressure at a site related to the evaluation of rubber wear of the contact patch portion of the tire is measured, a pressing load setting step in which setting is performed such that the contact pressure is applied to a sample as a pressing load, a setting step in which the sample frictional energy of a sample of the same material as that of the tire is determined under sample input conditions set based on the tire frictional energy under each of the measured tire input conditions in a state in which the pressing load is applied to the sample, and a measurement condition for measuring the sample wear amount of the sample is set based on the tire frictional energy under each of the measured tire input conditions and the sample frictional energy determined under each of the sample input conditions, a sample wear amount measurement step in which the sample wear amount of the sample is measured by a wear amount measurement device under the set measurement condition and a rubber index calculation step in which the rubber index of the tire is calculated based on the measured sample frictional energy and the sample wear amount.

In the present invention, the setting step preferably comprises a step in which a frictional energy function representing the correspondence relationships between the tire input condition and the tire frictional energy is calculated for each of the types of the tire input conditions, a step in which an expected value of the tire frictional energy is calculated based on the frequency data representing the relationship between the tire input measured during practical vehicle travel using the tire and the frequency of the tire input, and on the frictional energy function for each of the tire input conditions, a sample input condition setting step which sets sample input conditions which are provided to the sample for measuring the sample frictional energy of the sample by the frictional energy measurement device, a sample frictional energy measurement step in which the sample frictional energy of the sample is measured under the set sample input conditions, and the sample frictional energy is measured while changing the sample input conditions until the measured sample frictional energy corresponds to the expected value of the tire frictional energy and a sample wear amount measurement condition setting step in which the measured sample frictional energy sets a sample input condition corresponding to the expected value of the tire frictional energy as a measurement condition for measuring the sample wear amount, wherein, in the sample wear amount measurement step, the sample wear amount of the sample is measured under a measurement condition set in the sample wear amount measurement condition setting step.

In the present invention, the setting step preferably comprises, for each of the plural tire input conditions, a sample input condition setting step which sets sample input conditions which are provided to the sample for measuring the sample frictional energy of the sample by the frictional energy measurement device, a sample frictional energy measurement step in which the sample frictional energy of the sample is measured under the set sample input conditions, and the sample frictional energy is measured while changing the sample input conditions until the measured sample frictional energy corresponds to the tire frictional energy measured by the corresponding tire input condition and a sample wear amount measurement condition setting step in which the measured sample frictional energy sets a sample input condition corresponding to the tire frictional energy measured under the corresponding tire input condition as a measurement condition for measuring the sample wear amount, wherein, for each of the plural tire input conditions, in the sample wear amount measurement step, the sample wear amount of the sample is measured under a measurement condition set in the sample wear amount measurement condition setting step, and the rubber index calculation step comprises, for each of the plural tire input conditions, a step of calculating rubber index based on the frictional energy and the sample wear amount, a step of calculating for each of the types of the tire input conditions, the rubber index function representing the correspondence relationships between the tire input condition and the tire rubber index based on the rubber index calculated for each of the plural tire input conditions and a step of calculating the expected value of the rubber index based on frequency data representing the relationship between the tire input measured during practical vehicle travel using the tire and frequency of the tire input, and on rubber index function for each of the tire input conditions.

Further, in the present invention, the setting step preferably comprises a step in which a frictional energy function representing the correspondence relationships between the tire input condition and the tire frictional energy is calculated for each of the types of the tire input conditions, a step in which an expected value of the tire frictional energy is calculated based on the frequency data representing the relationship between the tire input measured during practical vehicle travel using the tire and the frequency of the tire input, and on the frictional energy function for each of the tire input conditions, a sample input condition setting step which sets sample input conditions which are provided to the sample for computing the sample frictional energy of the sample by a sample model of the sample, a sample frictional energy computing step in which the sample frictional energy of the sample is computed under the set sample input conditions, and the sample frictional energy is computed while changing the sample input conditions until the computed sample frictional energy corresponds to the expected value of the tire frictional energy and a sample wear amount measurement condition setting step in which the computed sample frictional energy sets a sample input condition corresponding to the expected value of the tire frictional energy as a measurement condition for measuring the sample wear amount, wherein, in the sample wear amount measurement step, the sample wear amount of the sample is measured under a measurement condition set in the sample wear amount measurement condition setting step.

Further, in the present invention, the setting step preferably comprises, for each of the plural tire input conditions, a sample input condition setting step which sets sample input conditions which are provided to the sample for computing the sample frictional energy of the sample based on the sample model of the sample, a sample frictional energy computing step in which the sample frictional energy of the sample is computed under the set sample input conditions, and the sample frictional energy is computed while changing the sample input conditions until the computed sample frictional energy corresponds to the tire frictional energy measured by the corresponding tire input condition and a sample wear amount measurement condition setting step in which the measured sample frictional energy sets a sample input condition corresponding to the tire frictional energy measured under the corresponding tire input condition as a measurement condition for measuring the sample wear amount, wherein, for each of the plural tire input conditions, in the sample wear amount measurement step, the sample wear amount of the sample is measured under a measurement condition set in the sample wear amount measurement condition setting step, and the rubber index calculation step comprises, for each of the plural tire input conditions, a step of calculating rubber index based on the frictional energy and the sample wear amount, a step of calculating for each of the types of the tire input conditions, the rubber index function representing the correspondence relationships between the tire input condition and the tire rubber index based on the rubber index calculated for each of the plural tire input conditions and a step of calculating the expected value of the rubber index based on frequency data representing the relationship between the tire input measured during practical vehicle travel using the tire and frequency of the tire input, and on rubber index function for each of the tire input conditions.

A rubber index calculation device of a tire of the present invention comprises a tire frictional energy measurement means in which a tire frictional energy of a tire under plural tire input conditions which are provided to the tire is measured by a frictional energy measurement device which performs measurement based on the shearing force and the slippage of a tire contact patch, a contact pressure measurement means in which a contact pressure at a site related to the evaluation of rubber wear of the contact patch portion of the tire is measured, a pressing load setting means in which setting is performed such that the contact pressure is applied to a sample as a pressing load, a setting means in which the sample frictional energy of a sample of the same material as that of the tire is determined under sample input conditions set based on the tire frictional energy under each of the measured tire input conditions in a state in which the pressing load is applied to the sample, and a measurement condition for measuring the sample wear amount of the sample is set based on the tire frictional energy under each of the measured tire input conditions and the sample frictional energy determined under each of the sample input conditions, a sample wear amount measurement means in which the sample wear amount of the sample is measured by a wear amount measurement device under the set measurement condition and a rubber index calculation means in which the rubber index of the tire is calculated based on the measured sample frictional energy and the sample wear amount.

A tire rubber index calculation program of the present invention is characterized in that the program allows a computer to execute a processing comprising a tire frictional energy measurement step in which a tire frictional energy of a tire under plural tire input conditions which are provided to the tire is measured by a frictional energy measurement device which performs measurement based on the shearing force and the slippage of a tire contact patch, a contact pressure measurement step in which a contact pressure at a site related to the evaluation of rubber wear of the contact patch portion of the tire is measured, a pressing load setting step in which setting is performed such that the contact pressure is applied to a sample as a pressing load, a setting step in which the sample frictional energy of a sample of the same material as that of the tire is determined under sample input conditions set based on the tire frictional energy under each of the measured tire input conditions in a state in which the pressing load is applied to the sample, and a measurement condition for measuring the sample wear amount of the sample is set based on the tire frictional energy under each of the measured tire input conditions and the sample frictional energy determined under each of the sample input conditions, a sample wear amount measurement step in which the sample wear amount of the sample is measured by a wear amount measurement device under the set measurement condition and a rubber index calculation step in which the rubber index of the tire is calculated based on the measured sample frictional energy and the sample wear amount.

Effects of the Invention

By the present invention, it becomes possible to provide a method of testing rubber wear in which a wear phenomenon occurred in a tire can be precisely reproduced in a sample, and a method, a device and a program of calculating the rubber index of a tire using the method of testing rubber wear.

BRIEF DESCRIPTION OF DRAWINGS

FIG. 3 (A) represents a perspective view illustrating one example of a sample, and FIG. 3 (B) represents a diagram illustrating characteristics of the shearing force of the sample.

MODES FOR CARRYING OUT THE INVENTION

A method of testing rubber wear of the present invention will now be described in detail.

Figure 1:
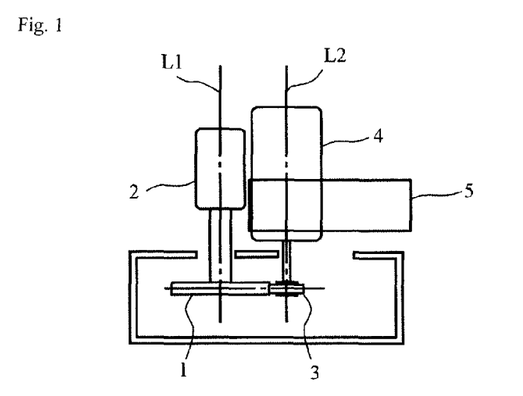
FIG. 1 represents a schematic view illustrating one example of a preferred embodiment of a method of testing rubber wear of the present invention.

FIG. 1 represents a schematic view illustrating one example of a preferred embodiment of a method of testing rubber wear of the present invention. The illustrated example thereof is configured such that the method comprises a disk-shaped grinding wheel 1, a grinding wheel rotating means 2 which rotates the grinding wheel 1, a sample rotating means 4 which rotates a disk-shaped sample 3 around an axis L2 which is parallel to a rotation axis L1 of the grinding wheel 1 and a sample pressing means 5 which presses the sample 3 on the grinding wheel 1, and such that the sample 3 can be worn by rotating the grinding wheel 1 and the sample 3 while pressing the periphery of the sample 3 on the periphery of the grinding wheel 1.

In the present invention, it is important to apply a pressing load on the sample 3 such that the contact pressure when the sample 3 is pressed on the outer periphery of the grinding wheel 1 and the contact pressure at a site related to the evaluation of rubber wear of a contact patch portion of the tire are the same. By this, it becomes possible to precisely reproduce the rubber wear phenomenon occurred in a tire in the sample 3.

In the method of testing rubber wear of the present invention, for example, by setting the pressing load such that the contact pressure at a tire center portion and the contact pressure when the sample 3 is pressed on the outer periphery of the grinding wheel 1 are the same, the rubber wear phenomenon occurred at the tire center portion can be precisely reproduced in the sample 3, whereby the wear life of a tire can be precisely evaluated. By setting the pressing load such that the contact pressure at a tire shoulder portion and the contact pressure when the sample 3 is pressed on the outer periphery of the grinding wheel 1 are the same, the rubber wear phenomenon occurred at the tire shoulder portion can be precisely reproduced in the sample 3, whereby the partial wear properties can be precisely evaluated.

In the present invention, it is preferred that a torque be applied to the disk-shaped sample 3 such that the frictional energy generated when the disk-shaped sample 3 is pressed on the outer periphery of the grinding wheel 1 and the frictional energy at a site related to the evaluation of rubber wear of the contact patch portion of a tire are the same. As mentioned above, the dependence of the contact pressure on the wear properties of rubber is high. Accordingly, in order to more precisely reproduce the wear phenomenon at a site related to the evaluation of rubber wear of the contact patch of a tire by using the sample 3, it is preferred that the contact pressure at a site related to the evaluation of rubber wear of the contact patch of a tire and a pressing load when the sample 3 is pressed on the outer periphery of the grinding wheel 1 are made the same, and further, a torque is set such that the frictional energy generated when the disk-shaped sample 3 is pressed on the outer periphery of the grinding wheel 1 and the frictional energy at a site related to the evaluation of rubber wear of the contact patch of the tire are the same.

In the present invention, for the measurement of the contact pressure of a tire and a sample and the measurement of wear energy, known methods can be used. For example, a contact portion measurement device for tire contact patch described in Japanese Patent No. 3277155 and Japanese Patent No. 3406643 can be used. In the present embodiment, it is preferred that, when the frictional energy of the contact patch of a sample having considerably smaller size than that of the tire, not that of the tire itself, is measured, the resolution of a camera which photographs the contact patch of the sample or the sampling rate of photographing be made higher compared to the case when the frictional energy of the tire contact patch is measured.

When a method of testing rubber wear of the present invention is performed, a wear test device which measures wear amount of a tire by a so-called Lambourn test as described in Patent Document No. 3277155 and Japanese Unexamined Patent Application Publication No. 2006-242697 can be used.

Next, a calculating method of rubber index of the present invention will now be described. The calculating method of rubber index of the present invention is a method in which a sample wear amount is measured by using a method of testing rubber wear of the present invention and a rubber index is calculated based on the sample wear amount. The calculating method of rubber index of the present invention will be described in detail by taking the first to the fourth embodiments as examples.

(First Embodiment)

Figure 2:
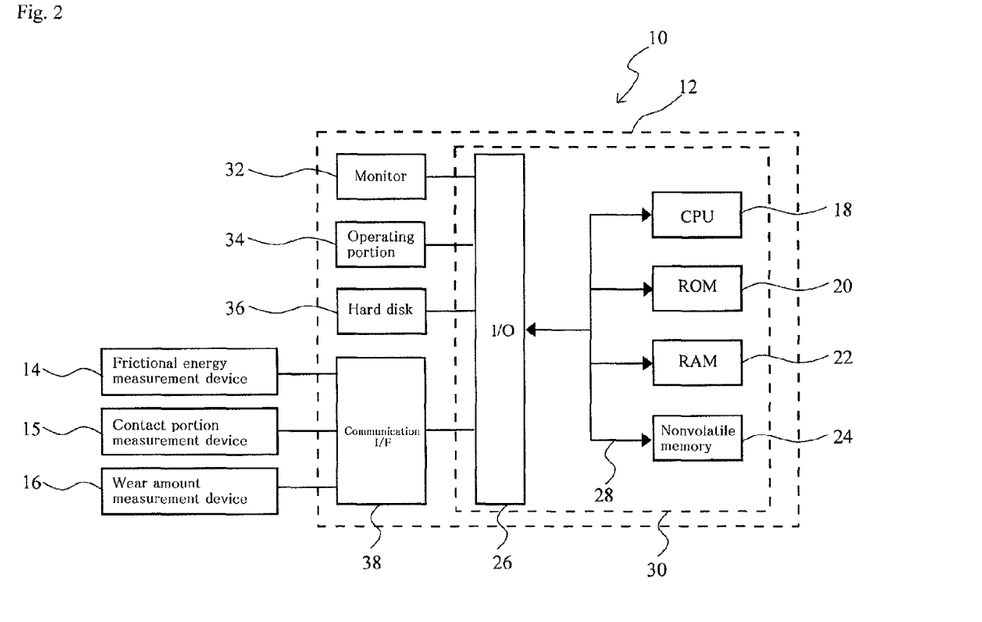
FIG. 2 represents a schematic block diagram of a rubber index calculation system.

FIG. 2 represents a schematic block diagram of a rubber index calculation system 10 according to the present embodiment. As illustrated in the same figure, a tire rubber index calculation system 10 is configured by comprising a tire rubber index calculation device 12, a frictional energy measurement device 14, a contact portion measurement device 15 and a wear amount measurement device 16.

As illustrated in FIG. 2, the tire rubber index calculation device 12 is configured by comprising a computer 30 to which a CPU (Central Processing Unit) 18, a ROM (Read Only Memory) 20, a RAM (Random Access Memory) 22, a non-volatile memory 24 and an input output interface (I/O) 26 are individually connected via a bus 28.

To I/O 26, an operating portion 34 composed of a monitor 32 composed of a liquid crystal display or the like, a keyboard, a mouse or the like, a hard disk 36 and a communication interface (I/F) 38 are connected. To a communication I/F 38, the frictional energy measurement device 14, a contact portion measurement device 15 and a wear amount measurement device 16 are connected.

The frictional energy measurement device 14 measures the frictional energy of the contact patch of, for example, a disk-shaped sample of a material same as that of the tread portion of a tire whose rubber index is an object of calculation. As such a device, a contact portion measurement device of a tire contact patch described, for example, in Japanese Patent No. 3277155 and Japanese Patent No. 3406643 can be used. In the present embodiment, it is preferred that, since the frictional energy of the contact patch of a sample having considerably smaller size than that of the tire, not that of the tire itself, is measured, the resolution of a camera which photographs the contact patch of the sample or the sampling rate of photographing be made higher compared to the case when the frictional energy of the tire contact patch is measured.

Figure 3:
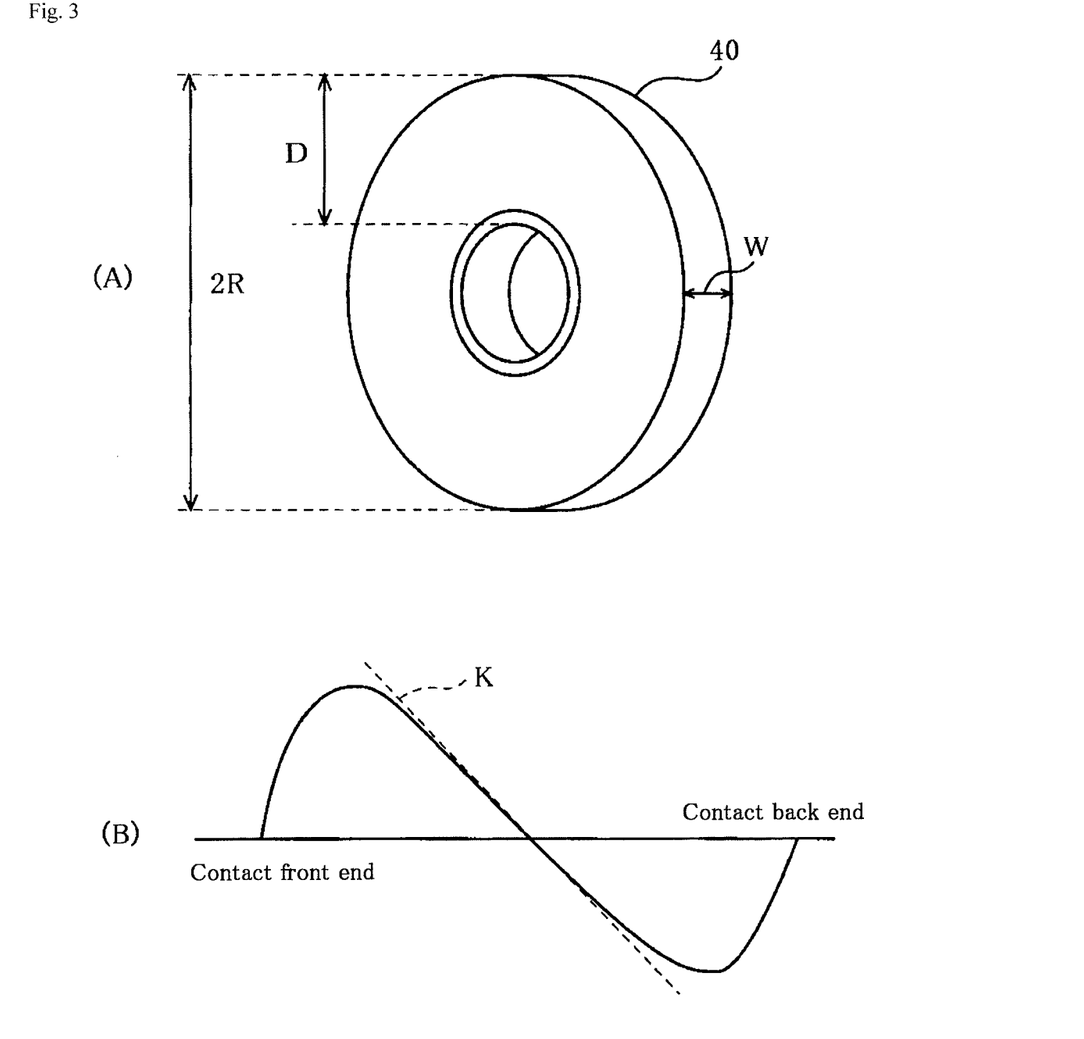

As the sample, for example, a sample 40 as illustrated in FIG. 3(A) is used. In this case, it is preferred that the width thereof be 5 mm or more, the diameter thereof 2R be less than 80 mm and the thickness (the outer diameter−the inner diameter of the sample 40) D thereof be 5 mm or more. As illustrated in FIG. 3(B), it is preferred that a sample whose shearing force gradient K be negative be used.

The contact portion measurement device 15 measures the contact pressure of a contact pressure and sample at a site related to the evaluation of rubber wear of a contact patch portion of a tire is measured. As the contact portion measurement device, a known device can be used, and examples thereof include contact portion measurement devices described in Japanese Patent No. 3277155 and Japanese Patent No. 3406643.

The wear amount measurement device 16 measures wear amount of a tire whose rubber index is an object of calculation. As such a device, a wear test device which measures wear amount of a tire by a so-called Lambourn test as described in U.S. Pat. No. 3,277,155 and Japanese Unexamined Patent Application Publication No. 2006-242697 can be used.

Next, a processing executed in a CPU 18 of the tire rubber index calculation device 12 is described with reference to the flow chart illustrated in FIG. 4. The program of the processing routine illustrated in FIG. 4 is, for example, prestored in the hard disk 36, and the processing routine is executed by reading out the program from the hard disk 36 by the CPU 18.

Figure 4:
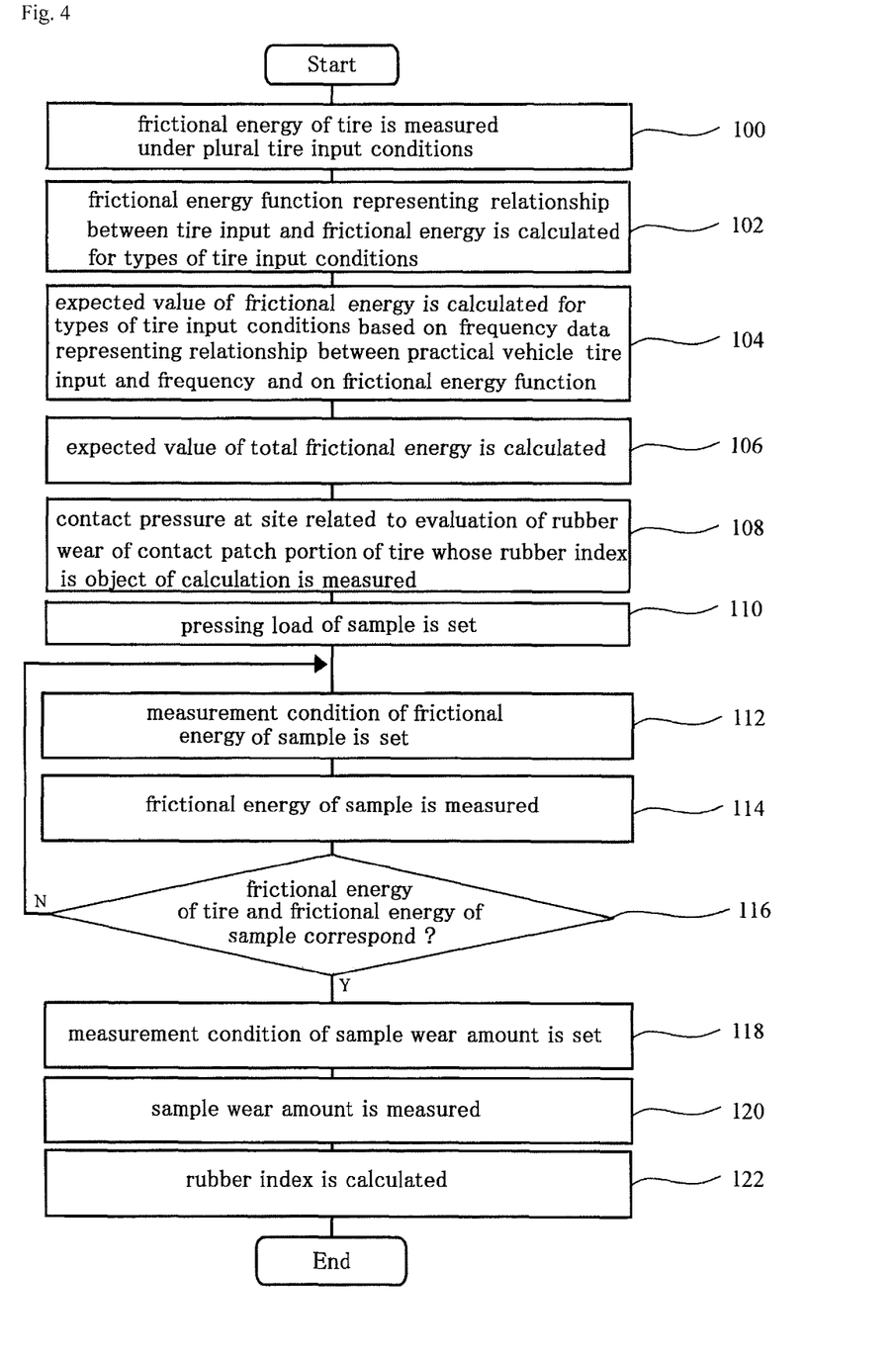
FIG. 4 represents a flow chart illustrating the flow of a rubber index calculation processing executed in a rubber index calculation device of the first embodiment.

In a step 100 illustrated in FIG. 4, the frictional energy measurement device 14 to which a tire whose rubber index is an object of calculation is set is instructed that the frictional energy of a tire whose rubber index is an object of calculation be measured under plural tire input conditions. Since example of the types of the tire input include a driving force (back and forth force) of a lateral force (right and left force) and a braking force, for each of these types of the tire input, plural tire input conditions are set. In the following, for the simplicity of the explanation, the case where a driving force and a lateral force are set as the tire input conditions will be described.

The frictional energy measurement device 14, when instructed the measurement from the rubber index calculation device 12, measures the frictional energy of a tire for each of the instructed plural tire input conditions. By this, for example, each frictional energy when plural different driving forces are applied to a tire and each frictional energy when plural different lateral forces are applied to a tire are individually measured by the frictional energy measurement device 14. The measured frictional energy is output to the rubber index calculation device 12.

In a step 102, the frictional energy function representing the correspondence relationships between the tire input and the frictional energy is calculated for each of the types of tire input conditions. That is, a frictional energy function f1 representing the correspondence relationships between the driving force and the frictional energy are calculated based on the frictional energy measured by applying different plural driving forces on a tire. The calculation of the frictional energy function is determined by using, for example, a method of least squares or the like. In the same manner as above, a frictional energy function f2 representing the correspondence relationships between the lateral force and the frictional energy is calculated.

In a step 104, the expected value of the frictional energy for each of the types of the tire input is calculated based on the frequency data representing the relationship between the tire input measured when a vehicle on which a tire whose rubber index is an object of calculation is provided practically travels on a predetermined travel course, and the frequency thereof, and on the frictional energy function determined in the step 102.

The frequency data is obtained, for example, by the following. First, a vehicle to which a sensor measuring a driving force and lateral force which are input to a tire is attached travels on the above-mentioned travel course, and the driving force and the lateral force during travelling are measured. Then, the frequency of each input is determined based on the date of the measured driving force and lateral force. By this, a frequency data representing the relationship between the driving force and the lateral force measured in a practical vehicle and the frequency (%) thereof is obtained. The obtained frequency data, for example, is prestored in the hard disk 36.

Then, the frictional energy corresponding to each driving force data when tire frictional energy of the frequency data is measured is individually calculated by the frictional energy function f1, and each calculated friction energy is multiplied by the corresponding frequency, then all of the products are added. By this, the expected value of the frictional energy of a driving force Ewd is calculated. For example, when the types of the frictional energy of the measured driving force are set to $Ewd_1, Ewd_2, \ldots Ewd_n$ (n is the number of the types of the frictional energy of the driving force) and the frequency thereof is set to $h_1, h_2 \ldots h_n$ (n is the number of the types of the frictional energy of the driving force), the expected value of the frictional energy function of the driving force Ewd is calculated by the following formula:

$$Ewd = Ewd_1 \times h_1 + Ewd_2 \times h_2 +, \ldots Ewd_n \times h_n \qquad (1).$$

For the lateral force, the frictional energy Ewc is determined in the same manner as above. That is, when the types of the measured the frictional energy of the lateral force is set to $Ewc_1, Ewc_2, \ldots Ewc_n$ (n is the number of the types of the frictional energy of the lateral force) and the frequency thereof is set to $h_1, h_2 \ldots h_n$ (n is the number of the types of the frictional energy of the lateral force), the expected value Ewc of the frictional energy function of the lateral force is calculated by the following formula:

$$Ewc = Ewc_1 \times h_1 + Ewc_2 \times h_2 +, \ldots Ewc_n \times h_n \qquad (2).$$

In the step 106, by adding the expected value of the frictional energy of the driving force determined in the step 104 and the expected value of the frictional energy of the lateral force Ewc, the total of the expected values of the frictional energy Ew is calculated.

In a step 108, the contact portion measurement device 15 to which a tire whose rubber index is an object of calculation is set is instructed that the contact pressure at site related to the evaluation of the rubber wear of a contact patch portion of a tire whose rubber index is an object of calculation be measured. The measured contact pressure is output to the rubber index calculation device 12.

In the step 110, in order to measure the frictional energy of a disk-shaped sample of a material same as that of the tread portion of a tire whose rubber index is an object of calculation, the pressing load is set such that the contact pressure of the sample and the contact pressure measured in the step 108 are the same.

In the step 112, based on the expected value Ew of the frictional energy determined in the step 106, a measurement condition is decided for measuring the frictional energy of a disk-shaped sample of a material same as that of the tread portion of a tire whose rubber index is an object of calculation. When this step is first executed, the driving force corresponding to the expected value Ewd of the frictional energy of the driving force and the lateral force corresponding to the expected value Ewc of the frictional energy of the lateral force determined in the step 106 are individually determined by using frictional energy functions f1 and f2, and the determined driving force and lateral force are set as the measurement conditions (sample input conditions) for measuring the frictional energy of the sample.

In the step 114, the frictional energy measurement device 14 in which a sample is set is instructed that the frictional energy of a sample be measured in the measurement condition set in the step 112. By this, the frictional energy measurement device 14 measures the frictional energy of the sample under the measurement condition instructed by the rubber index calculation device 12. The measurement of the frictional energy of this sample is performed by measuring the shearing force and the slippage applied to the contact patch of the sample and by determining the frictional energy based on these. The measured frictional energy is output to the rubber index calculation device 12.

In the step 116, whether the expected value Ew of the frictional energy of a tire decided in the step 106 and the frictional energy of the sample measured by the frictional energy measurement device 14 in the step 114 correspond or not is judged, and when they do not correspond, the process returns to the step 112 to change the measurement condition and the same process as the above is repeated. When the expected value Ew of the frictional energy of the tire and the frictional energy of the sample correspond, the process proceeds to the step 118. In this way, the processing of measuring the frictional energy of the sample by changing the measurement condition is repeated until the expected value Ew of the frictional energy of the sample and the frictional energy of the sample correspond.

In the step 118, the measurement condition under which the expected value Ew of the frictional energy of the tire and the frictional energy of the sample correspond is set as the measurement condition for measuring the sample wear amount.

In a step 120, the wear amount measurement device 16 is instructed that wear amount be measured under the measurement conditions set in the step 118, that is, under measurement conditions (pressing load, driving force and lateral force) under which the expected value Ew of the frictional energy of the tire and the frictional energy of the sample correspond. By this, the wear amount measurement device 16 measures the sample wear amount m under the measurement condition instructed by the rubber index calculation device 12. The measured wear amount m is output to the rubber index calculation device 12.

In a step 122, based on the determined expected value Ew of the frictional energy of the sample and the wear amount m, the rubber index G is calculated, the calculation result is output to, for example, a monitor 32 or the hard disk 36, and the calculation result are displayed on the monitor 32 or stored in the hard disk 36. The rubber index G is determined by the following formula:

$$G = m/Ew \qquad (3).$$

In this way, in the present embodiment, the contact pressure at a site related to the evaluation of rubber wear of the contact patch of a tire is measured by the contact portion measurement device 15; the frictional energy of the sample is measured by the frictional energy measurement device 14 which measures the frictional energy of the sample based on the shearing force and the slippage of the tire contact patch, in a state in which this contact pressure and the contact pressure of the sample correspond; the measurement condition of the sample is adjusted such that the measured frictional energy of the sample and the frictional energy of the tire correspond; and the rubber index is calculated based on the sample wear amount measured under this measurement condition and the frictional energy of the sample. For this reason, wear amount of the sample can be more precisely measured than in the method of evaluating rubber wear in which a practical contact pressure of a tire is not taken into consideration as in the conventional manner, whereby the rubber index can be precisely calculated.

(Second Embodiment)

Next, the second embodiment of the present invention will be described. The same portion as in the first embodiment is indicated by the same sign and the explanation thereof in detail is omitted.

In the first embodiment, the frictional energy function for each type of the tire input condition is determined and the expected value of the frictional energy of the total tire is determined and then the rubber index is calculated. In the present embodiment, the case in which the rubber index for each tire input condition is calculated and the expected value of the rubber index from these rubber indexes will be described.

Since the rubber index calculation device according to the present embodiment is the same as in the first embodiment, the explanation thereof is omitted.

Next, the processing executed in a CPU 18 of the tire rubber index calculation device 12 will be described with reference to the flow chart illustrated in FIG. 5. The processing routine illustrated in FIG. 5 is prestored, for example, in a hard disk 36, and the processing routine is executed by reading out the program from the hard disk 36 by the CPU 18.

Figure 5:
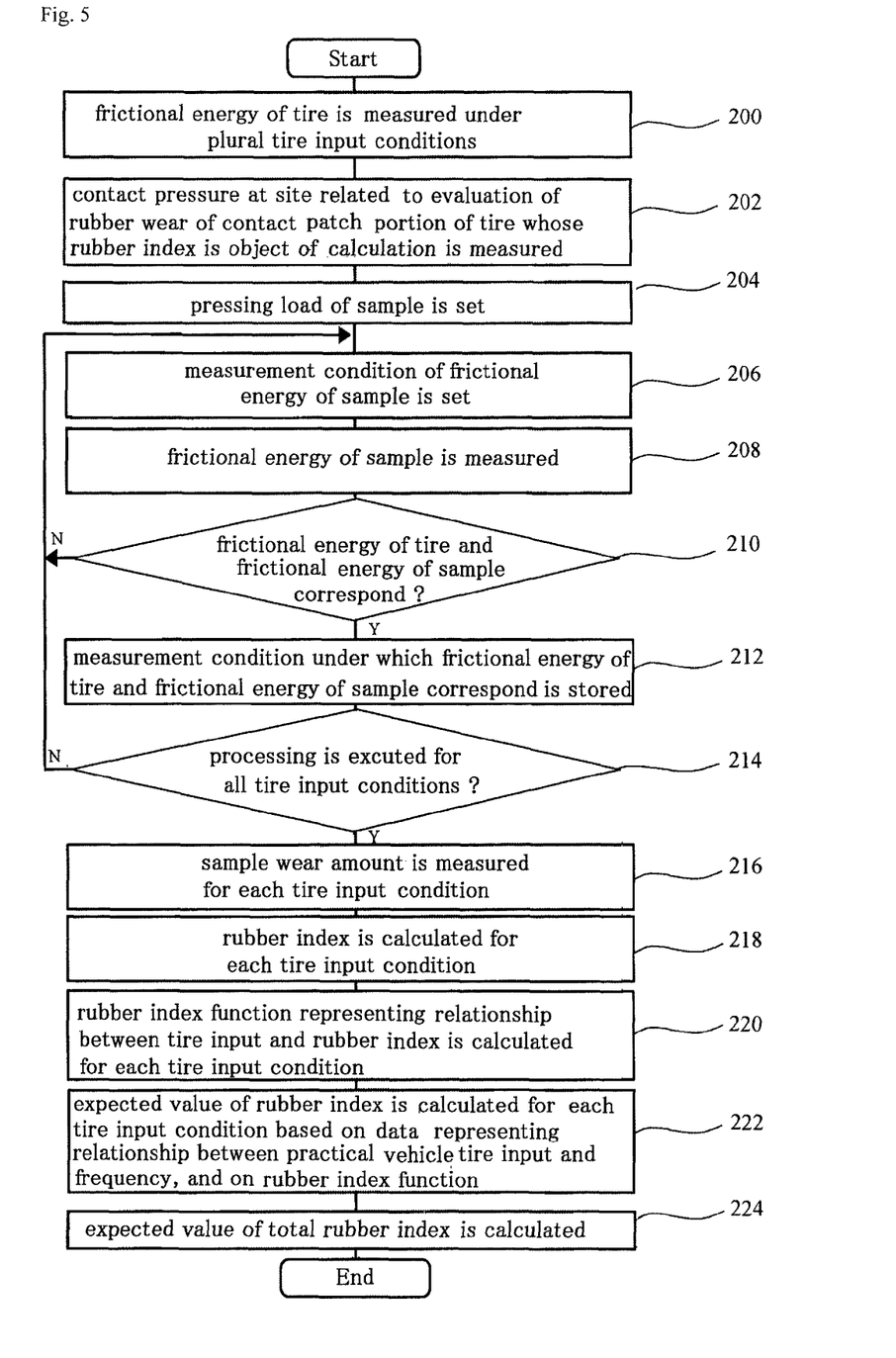
FIG. 5 represents a flow chart illustrating the flow of a rubber index calculation processing executed in a rubber index calculation device of the second embodiment.

In the step 200 illustrated in FIG. 5, in the same manner as in the step 100 in FIG. 4, the frictional energy measurement device 14 to which a tire whose rubber index is an object of calculation is set is instructed that the frictional energy of the tire whose rubber index is an object of calculation be measured under plural tire input conditions By this, the frictional energy measurement device 14 measures the frictional energy of a tire for each of the instructed plural tire input conditions instructed from the rubber index calculation device 12. By this, for example, each frictional energy when plural different driving forces are applied to a tire and each frictional energy when plural different lateral forces are applied to a tire are individually measured by the frictional energy measurement device 14. The measured frictional energy is output to the rubber index calculation device 12.

In a step 202, in the same manner as in the step 108, the contact portion measurement device 15 to which a tire whose rubber index is an object of calculation is set is instructed that the contact pressure at site related to the evaluation of the rubber wear of a contact patch portion of a tire whose rubber index is an object of calculation be measured. The measured contact pressure is output to the rubber index calculation device 12.

In the step 204, in order to measure the frictional energy of a disk-shaped sample of a material same as that of the tread portion of a tire whose rubber index is an object of calculation, the pressing load is set such that the contact pressure of the sample and the contact pressure measured in the step 202 are the same.

In the step 206, one of the plural tire input conditions under which the frictional energy is determined in the step 200 is set as the measurement condition for measuring the frictional energy of a sample.

In the step 208, the frictional energy measurement device 14 in which a sample is set is instructed that the frictional energy of a sample be measured in the measurement condition set in the step 206. By this, the frictional energy measurement device 14 measures the frictional energy of the sample under the measurement condition instructed by the rubber index calculation device 12. The measured frictional energy is output to the rubber index calculation device 12.

In the step 210, whether the frictional energy of a tire decided in the step 200 and the frictional energy of the sample measured by the frictional energy measurement device 14 in the step 208 correspond or not is judged, and when they do not correspond, the process returns to the step 206 to change the measurement condition and the same process as the above is repeated. When the frictional energy of the tire and the frictional energy of the sample correspond, the process proceeds to the step 212 to store the measurement condition in the hard disk 36. In this way, the processing of measuring the frictional energy of the sample by changing the measurement condition is repeated until the frictional energy of the sample and the frictional energy of the sample correspond.

In a step 214, for all the tire input conditions measured in the step 200, whether the above-mentioned processings of steps 206 to 212 are executed or not is judged, and when the processings are executed, the process proceeds to a step 216 and when there is any tire input conditions which are not yet executed, the processing returns to the step 206 to repeat the same processing as above. By this, each measurement condition for measuring the sample wear amount corresponding to each of the plural tire input conditions measured in the step 200 is set.

In step 216, the wear amount measurement device 16 is instructed that each wear amount be measured under measurement conditions (pressing load, driving force and lateral force) under which the frictional energy of the tire and the frictional energy of the sample correspond for each tire input condition. By this, the wear amount measurement device 16 individually measures the sample wear amount under each measurement condition instructed by the rubber index calculation device 12. The measured wear amount is output to the rubber index calculation device 12.

In the step 218, for each of the tire input conditions, the rubber index is individually calculated based on the frictional energy and the wear amount of the sample.

In a step 220, the rubber index function representing the correspondence relationships between the tire input and the rubber index is calculated for the types of the tire input conditions based on the rubber index for each of the tire input conditions determined in the step 218. That is, based on each rubber index calculated for the plural tire input conditions of driving force, a rubber index function f3 representing the correspondence relationships between the driving force and the rubber index is calculated. The calculation of the rubber index function f3 can be determined by using, for example, the method of least squares or the like. In the same manner, a rubber index function f4 representing the correspondence relationships between the lateral force and the rubber index is calculated. The calculation of these rubber index functions can be determined by using, for example, the method of least squares or the like.

In a step 222, the expected value of the rubber index for each of the types of the tire input is calculated based on the frequency data representing the relationship between the tire input measured when a vehicle on which a tire whose rubber index is an object of calculation is provided practically travels on a predetermined travel course, and the frequency thereof, and on the rubber index function for each of the types of the tire input conditions determined in the step 220.

Then, the rubber index corresponding to each driving force data when tire frictional energy of the frequency data is measured is individually calculated by the rubber index function f3, and each calculated rubber index is multiplied by the corresponding frequency, then all of the products are added. By this, the expected value of the rubber index of a driving force Gd is calculated. For example, when the types of the rubber index of the measured driving force are set to $Gd_1$, $Gd_2, \ldots Gd_n$ (n is the number of the types of the rubber index of the driving force) and the frequency thereof is set to $h_1$, $h_2 \ldots h_n$ (n is the number of the types of the rubber index of the driving force), the expected value of the rubber index of the driving force Gd is calculated by the following formula:

$$Gd = Gd_1 \times h_1 + Gd_2 \times h_2 +, \ldots Gd_n \times h_n \qquad (4).$$

For the lateral force, the rubber index Gc is determined in the same manner as above. That is, when the types of the measured the rubber index of the lateral force is set to $Gc_1$, $Gc_2, \ldots Gc_n$ (n is the number of the types of the rubber index of the lateral force) and the frequency thereof is set to $h_1$, $h_2 \ldots h_n$ (n is the number of the types of the rubber index of the lateral force), the expected value Gc of the rubber index of the lateral force is calculated by the following formula:

$$Gc = Gc_1 \times h_1 + Gc_2 \times h_2 +, \ldots Gc_n \times h_n \qquad (5).$$

In the step 224, by adding the expected value of the rubber index of the driving force determined in the step 222 and the expected value of the rubber index of the lateral force Gc, the total of the expected values of the rubber index G is calculated.

In this way, in the present embodiment, the contact pressure at a site related to the evaluation of rubber wear of the contact patch of a tire is measured by the contact portion measurement device 15; the frictional energy of the sample is measured by the frictional energy measurement device 14 which measures the frictional energy of the sample based on the shearing force and the slippage of the tire contact patch, in a state in which this contact pressure and the contact pressure of the sample correspond; the measurement condition of the sample is adjusted such that the measured frictional energy of the sample and the frictional energy of the tire correspond; and the rubber index is calculated based on the sample wear amount measured under this measurement condition and the frictional energy of the sample. For this reason, wear amount of the sample can be more precisely measured than in the method of evaluating rubber wear in which a practical contact pressure of a tire is not taken into consideration as in the conventional manner, whereby the rubber index can be precisely calculated.

(Third Embodiment)

Next, the third embodiment of the present invention will be described. The same portion as in the first embodiment is indicated by the same sign and the explanation thereof in detail is omitted.

In the first embodiment, the frictional energy of a sample is measured by the frictional energy measurement device 14. In the present embodiment, explained is the case where the frictional energy of the contact patch of the sample is determined by a simulation using the finite element method (FEM) by using a sample model in which the sample is divided into plural elements.

Since the rubber index calculation device according to the present embodiment is the same as in the first embodiment, the explanation thereof is omitted.

Figure 6:
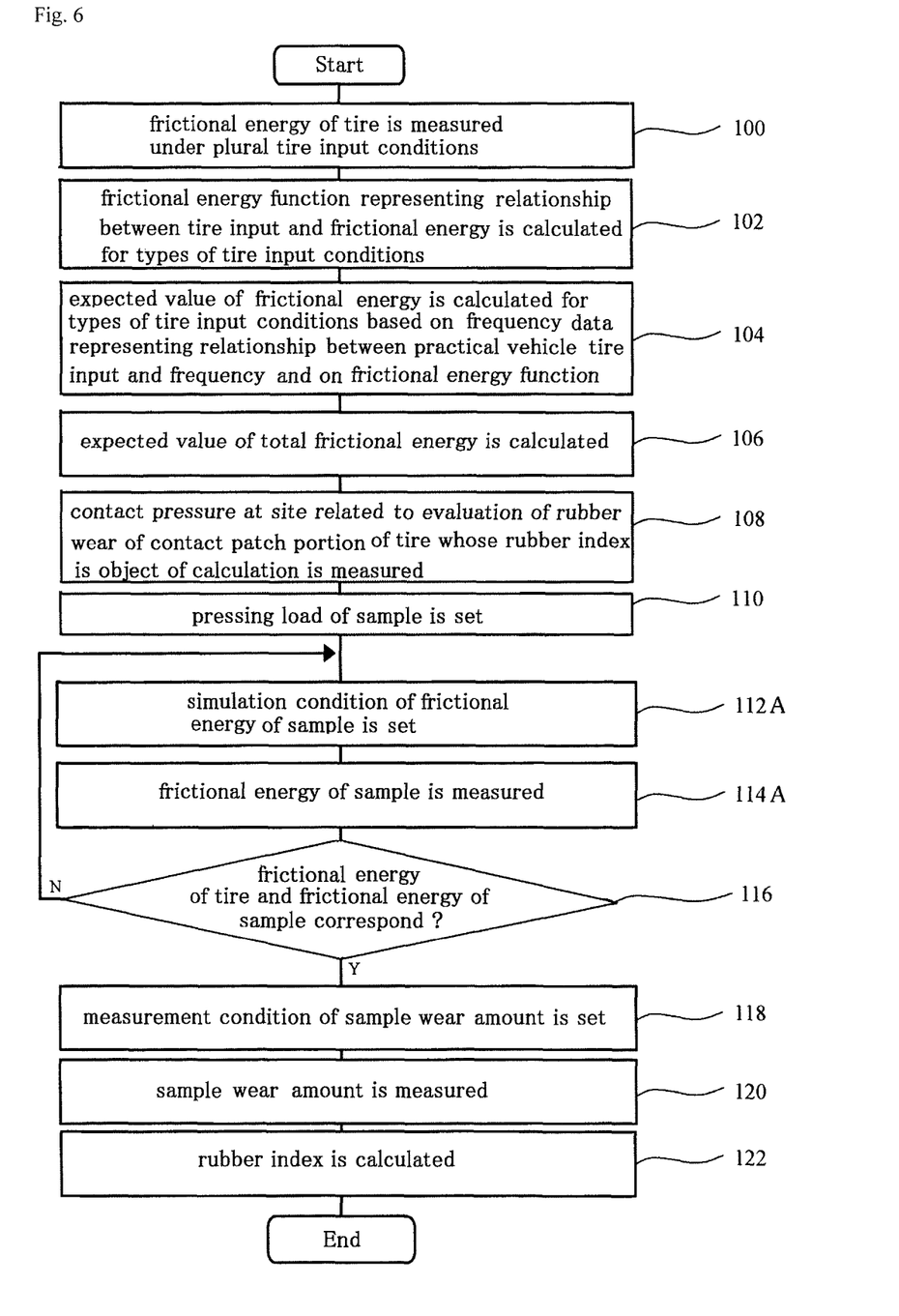
FIG. 6 represents a flow chart illustrating the flow of a rubber index calculation processing executed in a rubber index calculation device of the third embodiment.

Next, the processing executed in a CPU 18 of the tire rubber index calculation device 12 will be described with reference to the flow chart illustrated in FIG. 6. The processing routine illustrated in FIG. 6 is prestored, for example, in a hard disk 36, and the processing routine is executed by reading out the program from the hard disk 36 by the CPU 18. The sign of a processing step different from that in the flow chart in the FIG. 4 is denoted as 'A', and the same processing refers to the same sign, and the explanation thereof in detail is omitted.

Since the steps 100 to 110 are the same processings as illustrated in FIG. 4, the explanation thereof is omitted.

In the step 112A, based on the expected value Ew of the frictional energy determined in the step 106, a simulation condition is decided for simulating the frictional energy of a disk-shaped sample of a material same as that of the tread portion of a tire whose rubber index is an object of calculation. When this step is first executed, the driving force corresponding to the expected value Ewd of the frictional energy of the driving force and the lateral force corresponding to the expected value Ewc of the frictional energy Ewc of the lateral force determined in the step 106 are individually determined by using frictional energy functions f1 and f2, and the determined driving force and lateral force are set as the simulation conditions (sample input conditions) for simulating the frictional energy of the sample.

In a step 114A, the frictional energy of a sample is simulated under simulation conditions set in the step 106. For example, a sample model in which the sample is subjected to mesh division into plural elements is created, and by a rolling motion analysis of the sample model under the simulation conditions set in the step 106 by a known method using the finite element method, the shearing force and the slippage of the contact patch of the sample is determined. Based on the determined shearing force and slippage, the frictional energy of the sample is calculated.

Since the steps 116 to 122 are the same processings as illustrated in FIG. 4 except that the frictional energy of the tire used in the processing is the frictional energy calculated by a simulation, the explanation thereof is omitted.

In this way, in the present embodiment, the contact pressure at a site related to the evaluation of rubber wear of the contact patch of a tire is measured by the contact portion measurement device 15; the frictional energy of the sample is calculated based on the shearing force and the slippage of the tire contact patch determined by a simulation, in a state in which this contact pressure and the contact pressure of the sample correspond; the simulation condition of the sample is adjusted such that the calculated frictional energy of the sample and the frictional energy of the tire correspond; and the rubber index is calculated based on the sample wear amount measured under this condition and the frictional energy of the sample. For this reason, wear amount of the sample can be more precisely measured than in the method of evaluating rubber wear in which a practical contact pressure of a tire is not taken into consideration as in the conventional manner, whereby the rubber index can be precisely calculated.

(Fourth Embodiment)

Next, the fourth embodiment of the present invention will be described. The same portion as in the second embodiment is indicated by the same sign and the explanation thereof in detail is omitted.

In the second embodiment, the frictional energy of a sample is measured by the frictional energy measurement device 14. In the present embodiment, explained is the case where the frictional energy of the contact patch of the sample is determined by a simulation using the finite element method by using a sample model in which the sample is divided into plural elements.

Since the rubber index calculation device according to the present embodiment is the same as in the first embodiment, the explanation thereof is omitted.

Figure 7:
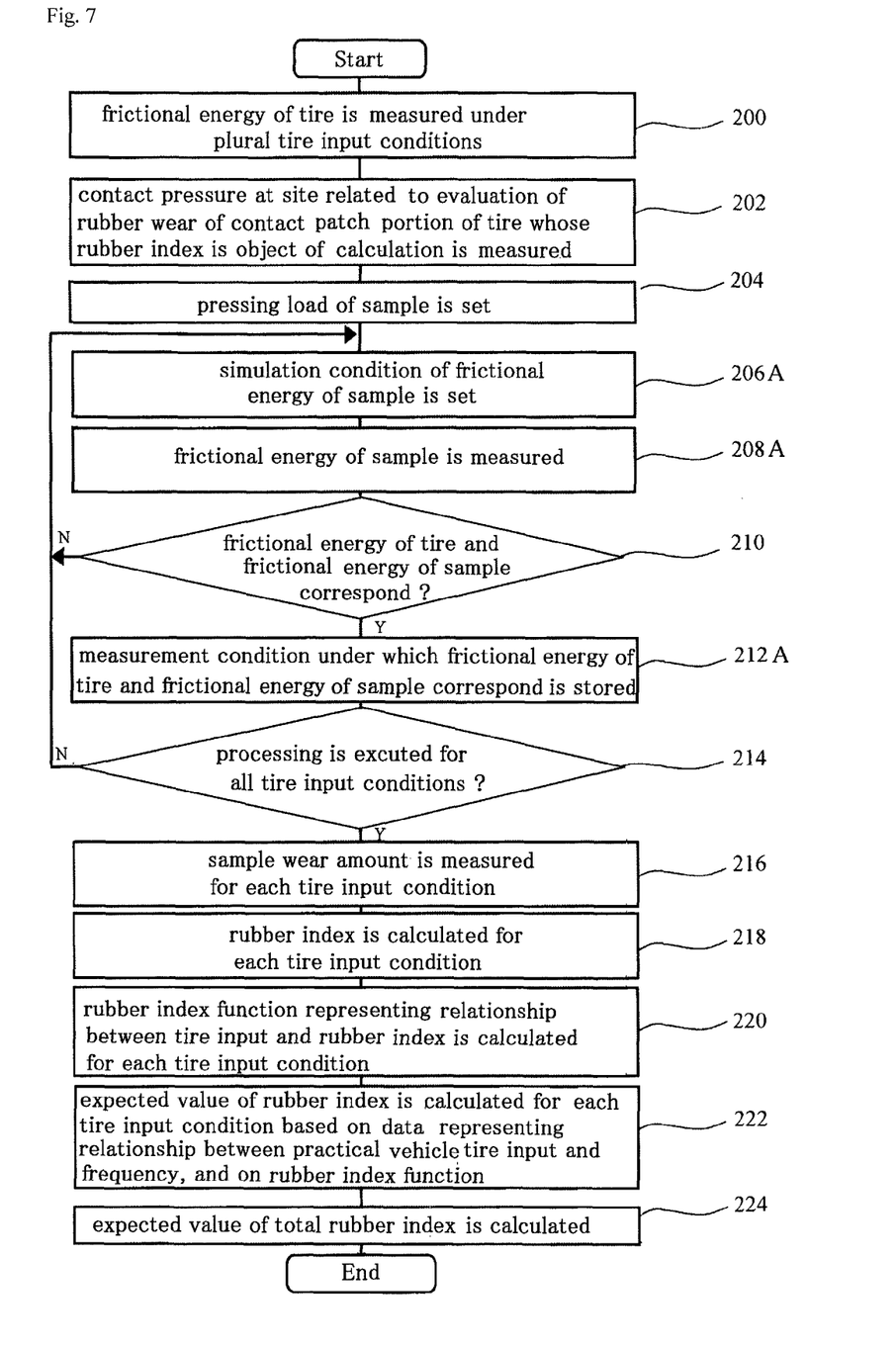
FIG. 7 represents a flow chart illustrating the flow of a rubber index calculation processing executed in a rubber index calculation device of the fourth embodiment.

Next, the processing executed in a CPU 18 of the tire rubber index calculation device 12 will be described with reference to the flow chart illustrated in FIG. 7. The processing routine illustrated in FIG. 7 is prestored, for example, in a hard disk 36, and the processing routine is executed by reading out the program from the hard disk 36 by the CPU 18. The sign of a processing step different from that in the flow chart in the FIG. 5 is denoted as 'A', and the same processing refers to the same sign, and the explanation thereof in detail is omitted.

Since the steps 200 to 204 illustrated in FIG. 7 are the same as the steps 200 to 204 illustrated in FIG. 5, the explanation thereof is omitted.

In the step 206A, one of the plural tire input conditions under which the frictional energy is determined in the step 200 is set as the simulation condition for simulating the frictional energy of a sample.

In the step 208A, in the same manner as in the step 114A in FIG. 6, the frictional energy of the sample is calculated by simulation under the simulation conditions set in the step 206A.

In the step 210, whether the frictional energy of a tire decided in the step 200 and the frictional energy of the sample calculated in the step 208A correspond or not is judged, and when they do not correspond, the process returns to the step 206A to change the measurement condition and the same process as the above is repeated. When the frictional energy of the tire and the frictional energy of the sample correspond, the process proceeds to the step 212A to store the simulation condition in the hard disk 36. In this way, the processing of simulating the frictional energy of the sample by changing the simulation condition is repeated until the frictional energy of the sample and the frictional energy of the sample correspond.

In a step 214, for all the tire input conditions measured in the step 200, whether the above-mentioned processings of steps 206A to 212A are executed or not is judged, and when the processings are executed, the process proceeds to a step 216 and when there is any tire input conditions which are not yet executed, the processing returns to the step 206A to repeat the same processing as above. By this, each measurement condition for measuring the sample wear amount corresponding to each of the plural tire input conditions measured in the step 200 is set.

Since the steps 216 to 224 are the same processings as illustrated in FIG. 5 except that the frictional energy of the tire used in the processing is the frictional energy calculated by a simulation, the explanation thereof is omitted.

In this way, in the present embodiment, the contact pressure at a site related to the evaluation of rubber wear of the contact patch of a tire is measured by the contact portion measurement device 15; the frictional energy of the sample is calculated by a simulation based on the shearing force and the slippage of the tire contact patch, in a state in which this contact pressure and the contact pressure of the sample correspond; the simulation condition of the sample is adjusted such that the calculated frictional energy of the sample and the frictional energy of the tire correspond; and the rubber index is calculated based on the sample wear amount measured under this simulation condition and the frictional energy of the sample. For this reason, wear amount of the sample can be more precisely measured than in the method of evaluating rubber wear in which a practical contact pressure of a tire is not taken into consideration as in the conventional manner, whereby the rubber index can be precisely calculated.

EXAMPLE

The present invention will be described in detail by way of Examples.

Example

Figure 8:
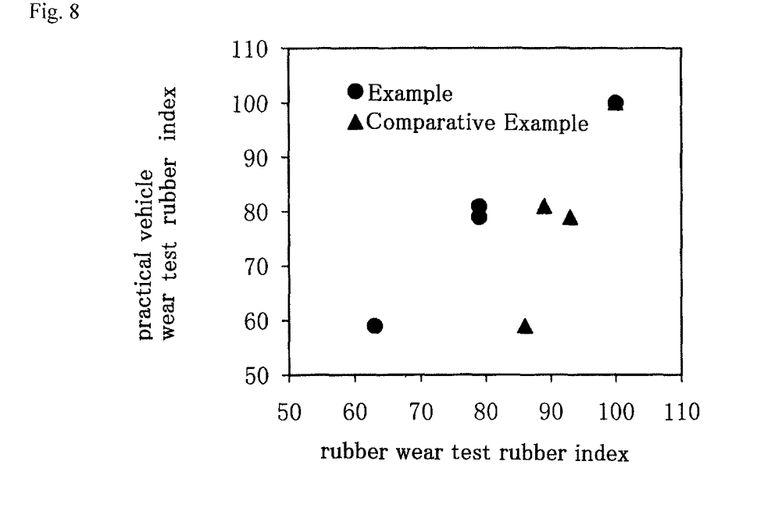
FIG. 8 represents a graph representing the relationship between the rubber wear test rubber index, which is an evaluation value related to tire wear determined by the actual measured result explained in the second embodiment and a conventional actual measured result, and the practical vehicle wear test rubber index, which is an evaluation value related to tire wear determined by tire wear amount or the like measured by practical vehicle travel.

For four types of tread rubbers having different rubber materials, the rubber wear test rubber index was calculated according to the second embodiment. The pressing load was a load setting (60N) adjusted to a center rib portion. The obtained rubber wear test rubber index was plotted with respect to the below-mentioned practical vehicle wear test index. The result is illustrated in FIG. 8.

Comparative Example

For the same four types of tread rubbers as in Example, the rubber index thereof was calculated. In Comparative Example, as the pressing load, the load setting (35N) assuming that the tire internal pressure be the contact pressure was used. The obtained rubber wear test rubber index was plotted with respect to the below-mentioned practical vehicle wear test rubber index. The result is illustrated in FIG. 8.
<Practical Vehicle Wear Test>

Tires using four types of tread rubbers used in Example were manufactured and fitted on a practical vehicle, and a practical vehicle travel was performed. The vehicle used for the practical vehicle was a front-wheel drive automobile, and tires whose wear amount is to be measured were fitted on the front tires. The tire size was 195/70R15, and the tire internal pressure was 360 kPa. The wear amount and the like was measured traveling at 0 to 100 km/h under conditions of a load of 15 kN. From the obtained wear amount, a practical vehicle wear test rubber index was determined.

In the Comparative Example, the order of the anti-wear properties in the result of practical vehicle wear test and the order of the anti-wear properties in the result of the prediction by the rubber wear test were observed to be reversed. Three kinds of rubbers exist around an index of 90 in the result of the rubber wear test. These indicate that although there were significant difference in the results of the practical vehicle wear test, the results of the rubber wear test were similar. On the other hand, the above-mentioned problem does not occur in Example. It was found that the order of anti-wear properties in a practical vehicle was precisely predicted.

DESCRIPTION OF SYMBOLS

1 GRINDING WHEEL
2 GRINDING WHEEL ROTATING MEANS
3 SAMPLE
4 SAMPLE ROTATING MEANS
5 SAMPLE PRESSING MEANS
10 TIRE RUBBER INDEX CALCULATION SYSTEM
12 TIRE RUBBER INDEX CALCULATION DEVICE
14 FRICTIONAL ENERGY MEASUREMENT DEVICE
15 CONTACT PORTION MEASUREMENT DEVICE
16 WEAR AMOUNT MEASUREMENT DEVICE
18 CPU
20 ROM
22 RAM
24 NONVOLATILE MEMORY
26 INPUT OUTPUT INTERFACE
28 BUS
30 COMPUTER
32 MONITOR
34 OPERATING PORTION
36 HARD DISK
38 COMMUNICATION INTERFACE

The invention claimed is:

1. A method for calculating a rubber index of a tire comprising
    a tire frictional energy measurement step in which a tire frictional energy of the tire under plural tire input conditions which are provided to the tire is measured by a frictional energy measurement device which performs measurement based on the shearing force and the slippage of the tire contact patch,
    a contact pressure measurement step in which a contact pressure at a site related to the evaluation of rubber wear of the contact patch portion of the tire is measured,
    a pressing load setting step in which setting is performed such that the contact pressure is applied to a sample as a pressing load,
    a setting step in which a sample frictional energy of the sample of the same material as that of the tire is determined under sample input conditions set based on the tire frictional energy under each of the measured tire input conditions in a state in which the pressing load is applied to the sample, and a measurement condition for measuring a sample wear amount of the sample is set based on the tire frictional energy under each of the measured tire input conditions and the sample frictional energy determined under each of the sample input conditions,
    a sample wear amount measurement step in which the sample wear amount of the sample is measured by a wear amount measurement device under the set measurement condition and
    a rubber index calculation step in which the rubber index of the tire is calculated based on the measured sample frictional energy and the sample wear amount.

2. The method for calculating a rubber index of a tire according to claim 1, wherein
    the setting step comprises
    a step in which a frictional energy function representing the corresponding relationships between the tire input condition and the tire frictional energy is calculated for each of the types of the plural tire input conditions, a step in which an expected value of a tire frictional energy is calculated based on a frequency data representing the relationship between the tire input measured during vehicle travel using the tire and the frequency of the tire input, and on the frictional energy function for each of the plural tire input conditions, a sample input condition setting step which sets the sample input conditions which are provided to the sample for measuring the sample frictional energy of the sample by the frictional energy measurement device, a sample frictional energy measurement step in which the sample frictional energy of the sample is measured under the set sample input conditions, and the sample frictional energy is measured while changing the sample input conditions until the measured sample frictional energy corresponds to the expected value of the tire frictional energy and a sample wear amount measurement condition setting step in which the measured sample frictional energy sets a sample input condition corresponding to the expected value of the tire frictional energy as a measurement condition for measuring the sample wear amount, wherein, in the sample wear amount measurement step, the sample wear amount of the sample is measured under a measurement condition set in the sample wear amount measurement condition setting step.

3. The method for calculating a rubber index of a tire according to claim 1, wherein the setting step comprises, for each of the plural tire input conditions, a sample input condition setting step which sets the sample input conditions which are provided to the sample for measuring the sample frictional energy of the sample by the frictional energy measurement device, a sample frictional energy measurement step in which the sample frictional energy of the sample is measured under the set sample input conditions, and the sample frictional energy is measured while changing the sample input conditions until the measured sample frictional energy corresponds to the tire frictional energy measured by the corresponding tire input condition and a sample wear amount measurement condition setting step in which the measured sample frictional energy sets a sample input condition corresponding to the tire frictional energy measured under the corresponding tire input condition as a measurement condition for measuring the sample wear amount, wherein, for each of the plural tire input conditions, in the sample wear amount measurement step, the sample wear amount of the sample is measured under a measurement condition set in the sample wear amount measurement condition setting step, and the rubber index calculation step comprises, for each of the plural tire input conditions, a step of calculating rubber index based on the frictional energy and the sample wear amount, a step of calculating for each of the types of the plural tire input conditions, a rubber index function representing the corresponding relationships between the tire input condition and the tire rubber index based on the rubber index calculated for each of the plural tire input conditions and a step of calculating the expected value of the rubber index based on frequency data representing the relationship between the tire input measured during vehicle travel using the tire and frequency of the tire input, and on rubber index function for each of the plural tire input conditions.

4. The method for calculating a rubber index of a tire according to claim 1, wherein the setting step comprises a step in which a frictional energy function representing the corresponding relationships between the tire input condition and the tire frictional energy is calculated for each of the types of the plural tire input conditions, a step in which an expected value of the tire frictional energy is calculated based on a frequency data representing the relationship between the tire input measured during vehicle travel using the tire and the frequency of the tire input, and on the frictional energy function for each of the plural tire input conditions, a sample input condition setting step which sets the sample input conditions which are provided to the sample for computing the sample frictional energy of the sample by a sample model of the sample, a sample frictional energy computing step in which the sample frictional energy of the sample is computed under the set sample input conditions, and the sample frictional energy is computed while changing the sample input conditions until the computed sample frictional energy corresponds to the expected value of the tire frictional energy and a sample wear amount measurement condition setting step in which the computed sample frictional energy sets a sample input condition corresponding to the expected value of the tire frictional energy as a measurement condition for measuring the sample wear amount, wherein, in the sample wear amount measurement step, the sample wear amount of the sample is measured under a measurement condition set in the sample wear amount measurement condition setting step.

5. The method index calculating a rubber index of a tire according to claim 1, wherein the setting step comprises, for each of the plural tire input conditions, a sample input condition setting step which sets sample input conditions which are provided to the sample for computing the sample frictional energy of the sample based on a sample model of the sample, a sample frictional energy computing step in which the sample frictional energy of the sample is computed under the set sample input conditions, and the sample frictional energy is computed while changing the sample input conditions until the computed sample frictional energy corresponds to the tire frictional energy measured by a corresponding tire input condition and a sample wear amount measurement condition setting step in which the measured sample frictional energy sets a sample input condition corresponding to the tire frictional energy measured under the corresponding tire input condition as a measurement condition for measuring the sample wear amount, wherein, for each of the plural tire input conditions, in the sample wear amount measurement step, the sample wear amount of the sample is measured under a measurement condition set in the sample wear amount measurement condition setting step, and the rubber index calculation step comprises, for each of the plural tire input conditions, a step of calculating rubber index based on a frictional energy and the sample wear amount, a step of calculating for each of the types of the plural tire input conditions, a rubber index function representing the corresponding relationships between the tire input condition and the tire rubber index based on the rubber index calculated for each of the plural tire input conditions and a step of calculating the expected value of the rubber index based on frequency data representing the relationship between the tire input measured during vehicle travel using the tire and frequency of the tire input, and on rubber index function for each of the plural tire input conditions.

6. A rubber index calculation device of a tire comprising a tire frictional energy measurement means in which a tire frictional energy of the tire under plural tire input conditions which are provided to the tire is measured by a frictional energy measurement device which performs measurement based on the shearing force and the slippage of the tire contact patch, a contact pressure measurement means in which a contact pressure at a site related to the evaluation of rubber wear of the contact patch portion of the tire is measured, a pressing load setting means in which setting is performed such that the contact pressure is applied to a sample as a pressing load, a setting means in which a sample frictional energy of the sample of the same material as that of the tire is determined under sample input conditions set based on the tire frictional energy under each of the measured tire input conditions in a state in which the pressing load is applied to the sample, and a measurement condition for measuring a sample wear amount of the sample is set based on the tire frictional energy under each of the measured tire input conditions and the sample frictional energy determined under each of the sample input conditions, a sample wear amount measurement means in which the sample wear amount of the sample is measured by a wear amount measurement device under the set measurement condition and a rubber index calculation means in which a rubber index of the tire is calculated based on the measured sample frictional energy and the sample wear amount.

* * * * *